(12) United States Patent
Hilscher et al.

(10) Patent No.: US 7,120,960 B2
(45) Date of Patent: Oct. 17, 2006

(54) ELECTRIC TOOTHBRUSHES

(75) Inventors: Alexander Hilscher, Kronberg (DE); Hansjörg Reick, Steinbach (DE)

(73) Assignee: Braun GmbH, Kronberg (DE)

( * ) Notice: Subject to any disclaimer, the term of this patent is extended or adjusted under 35 U.S.C. 154(b) by 429 days.

(21) Appl. No.: 10/310,599

(22) Filed: Dec. 5, 2002

(65) Prior Publication Data

US 2003/0131427 A1    Jul. 17, 2003

Related U.S. Application Data

(63) Continuation of application No. PCT/EP01/14430, filed on Dec. 8, 2001.

(30) Foreign Application Priority Data

Feb. 8, 2001  (DE)  ................................ 101 05 764

(51) Int. Cl.
*A46B 13/00*    (2006.01)

(52) U.S. Cl. ........................... 15/22.1; 15/22.2; 15/28; 15/105; 15/167.1

(58) Field of Classification Search ................. 15/22.1, 15/22.2, 28, 105, 167.1
See application file for complete search history.

(56) References Cited

U.S. PATENT DOCUMENTS 4,698,869 A * 10/1987 Mierau et al. ................ 15/22.1
5,815,872 A * 10/1998 Meginniss et al. ........... 15/22.1
5,974,615 A * 11/1999 Schwarz-Hartmann et al. ............................ 15/22.4

FOREIGN PATENT DOCUMENTS

| DE | 3117160 C2 | 4/1983 |
| DE | 4426446 A1 | 2/1995 |
| EP | 0158870 B1 | 3/1985 |
| WO | WO92/13499 | 8/1992 |
| WO | WO98/01083 | 1/1998 |

* cited by examiner

*Primary Examiner*—John Kim
*Assistant Examiner*—Abraham Bahta
(74) *Attorney, Agent, or Firm*—Fish & Richardson P.C.

(57) ABSTRACT

An electric toothbrush has a brush head which is mounted in a movable manner, and a drive for producing an oscillating operating movement in the brush head. The drive includes a cyclically movable drive part and a follower part. The follower part is biased against the drive part so that the follower part follows the drive part's cyclic drive movement. A sensor determines the brush head's contact pressure by sensing the extent of coupling between the follower part and the drive part, and determining the contact pressure of the brush head based on the extent of coupling.

19 Claims, 6 Drawing Sheets

ELECTRIC TOOTHBRUSHES

This is a continuation of PCT application Ser. No. PCT/EP01/14430, tiled Dec. 8, 2001, which claims priority from German application serial number 10105764.4, filed Feb. 8, 2001.

TECHNICAL FIELD

This invention relates to electric toothbrushes that sense contact pressure.

BACKGROUND

WO 98/01083 discloses a toothbrush with a brush-head carrier and a handle. The brush-head carrier is connected to, and projects out from, the handle. In the interior of the brush-head carrier is a drive shaft for driving the brush head. The drive shaft is mounted in a way that allows it to pivot in a rocking motion relative to the handle. The end of the brush-head carrier that is enclosed by the handle is biased against an eccentric by a spring. The toothbrush's drive motor drives the eccentric. Thus, the brush-head carrier follows the driven movement of the eccentric, making an oscillating rocking motion. As a result, the brush head moves in a reciprocating or picking fashion, thereby better removing impurities on the teeth, e.g., plaque.

Such a picking motion by the brush head, however, can irritate or even damage the gums. This irritation or damage is especially likely to occur when the brush head exerts excessive contact pressure against the teeth. Consequently, it has been proposed to equip the toothbrush with the ability to monitor contact pressure. A pressure sensor senses the contact pressure and indicates to the toothbrush operator whether cleaning is being carried out with the correct contact pressure. For example, WO 92/13499 provides a toothbrush with a drive shaft that can be pivoted out of a rest position, counter to a restoring force, transversely to the center longitudinal axis of the toothbrush. When the appropriate contact pressure has been reached, the toothbrush informs the toothbrush operator by means of acoustic or optical signals.

In other electric toothbrushes, such as those in DE 44 26 446 A1 and EP 0 158 870 B1, a pressure sensor measures the reaction force to the contact pressure. The pressure sensor is located on the brush-head carrier and/or the drive shaft.

The current solutions for sensing contact pressure employ relatively expensive and sensitive pressure sensors. Additionally, they use expensive signal-processing means. Sensing contact pressure in this way is especially difficult in the case of toothbrushes that execute a reciprocating or picking movement. A more simple solution is to sense contact pressure by using contacts that detect a cleaning-force threshold. However, such contacts only detect one cleaning-force threshold. In other words, they are not capable of notifying the operator both when the cleaning force has dropped below a lower limit and when it has exceeded an upper limit.

SUMMARY

In general, the invention features electric toothbrushes that sense contact pressure.

In one aspect, the invention features an electric toothbrush having a brush head, a drive that produces an oscillating motion in the brush head, and a sensor. The drive includes a cyclically movable drive part and a follower part that is connected to the brush head. The follower part is movably biased toward the drive part, and the sensor senses the contact between the drive part and the follower part.

In some embodiments, the sensor includes a pressure-determining circuit.

In another aspect, the invention features an electric toothbrush that senses the contact pressure exerted by its brush head. The toothbrush has a rotatable brush head, a drive that produces an oscillating movement in the brush head, and a sensor. The drive includes a cyclically movable drive part and a follower part that is connected to the brush head and is mounted in a movable manner. Additionally, a prestressing device biases the follower part against the drive part.

The toothbrush's sensor senses the extent of coupling between the follower part and the drive part. Based on the extent of coupling sensed, the sensor determines the contact pressure of the brush head. Increased contact pressure counteracts the biasing of the follower part against the drive part, and changes the amount of coupling between the follower part and the drive part. The follower part is subjected to the contact pressure of the brush head and is biased counter to the brush head. The result is that when a certain contact pressure is exceeded, the biasing is no longer sufficient to fully couple the follower part and the drive part.

The sensor determines the contact pressure of the brush head by sensing the extent to which the follower part follows the drive part. In some embodiments, the same result is achieved by biasing the drive part against the follower part. Preferably, though, the follower part is biased against the drive part. In some embodiments, movements other than cyclic drive movements may also be used.

In some embodiments, the prestressing device is designed such that, when the contact pressure is within a desired range, the follower part is only coupled to the drive part over part of the drive part's movement cycle. Over the rest of the movement cycle, the follower part is disengaged from the drive part, counter to the prestressing device, by the contact pressure.

In some embodiments, the toothbrush has three operating ranges. In the first operating range, the follower part engages fully with the drive part. The follower part follows the cyclic drive movement of the drive part directly (i.e., one to one). In the second operating range, the follower part only follows the drive part over a segment of the drive part's movement cycle. The follower part disengages from the drive part over the rest of the movement cycle. In the third operating range, the follower part and the drive part are fully uncoupled. Thus, the follower part does not follow the drive movement of the drive part at all.

Having these three ranges makes it possible for the sensor to sense both a lower limit value and an upper limit value for the desired contact pressure range. Additionally, the contact pressure may be sensed in quantitative terms within the desired range. The above-mentioned second operating range corresponds to the desired contact pressure range.

In some embodiments, the contact pressure is determined by a duty cycle. The duty cycle specifies the extent of coupling between the follower part and the drive part. The duty cycle is determined from the segments of the drive part's movement cycles during which the follower part follows the drive part's drive movement, and from the segments during which the follower part is uncoupled from the drive part. The duty cycle is a measure of the extent to which the follower part has moved out of step with the cyclic drive movement of the drive part. Consequently, the duty cycle is a measure of the contact pressure exerted by the brush head. Because the contact pressure is determined from a duty cycle, the contact pressure can be determined in quantitative terms via straightforward on/off sensing. The connection between the follower part and drive part is used as a switch.

In some embodiments, the duty cycle may be determined by only one movement cycle. In some cases, the duty cycle may also be averaged over a number of cycles, in order to reduce sensing tolerances and achieve higher measurement accuracy.

In some embodiments, the duty cycle is determined via time sensing. In other words, the time periods of the respective coupling states are sensed and compared to each other. In some cases, the duty cycle is measured by sensing the distances or angles of rotation covered during a movement cycle of the drive part, during which the corresponding coupling states are present. The distances or angles of rotation over this movement cycle are then compared to each other.

In some embodiments, the extent of coupling between the follower part and drive part is measured by sensing the electrically conductive contact between them. In some such embodiments, the follower part and the drive part are made of metal, and a voltage is applied to at least those sections of the drive part and follower part that are in contact with each other. As long as the two parts are in contact, an electric current flows. As soon as the two parts disengage, current no longer flows. Straightforward on/off sensing of the extent of coupling between the follower part and the drive part is thus provided, since a signal flow either flows or is interrupted. In other words, the follower part and the drive part together form a switch that may be used as a coupling sensor.

In some embodiments, the toothbrush includes a stroke drive. The stroke drive causes the brush head, which is mounted in a movable manner, to execute a reciprocating or picking movement. In some such embodiments, a cam is provided as the drive's cyclically movable drive part. The follower part rolls or slides on the curved surface of the cam. The cam can be driven in rotation, thereby acting as an eccentric, converting rotary movement into the reciprocating movement of the follower part. The sensing of the extent of coupling preferably occurs between the cam and the drive part. In some embodiments, the interface at which the extent of coupling is sensed is located at a different place in the drive train. It is preferable, however, for the biased connection between the cam and the drive part to be used to monitor the extent of coupling.

In some embodiments, the follower part is mounted in a movable manner and is connected to the brush head such that a movement of the follower part is transmitted to the brush head. Preferably, the entire brush-head carrier, in the interior of which a drive shaft may be provided, is mounted such that it can be pivoted like a rocker. In some cases, the follower part is an end arm part of the rocking arrangement, and is held under stress against the cam by means of a spring. In some cases, the brush-head carrier is mounted in a rigid manner relative to the handle and only the brush head is mounted such that it can be moved relative to the brush-head carrier. In some such cases, the follower part may be formed from a part of the drive train that is mounted in a movable manner in the interior of the brush-head carrier. In some embodiments, the drive spindle is mounted in a movable manner, in order to produce the stroke or picking movement of the brush head. In some such cases, the drive spindle forms the follower part, which is made to oscillate transversely by a corresponding cam.

In some embodiments of the invention, the cam is arranged on the drive part, which is mounted in a movable manner and connected to the brush head. The cam is run on a further driven drive part, which may be a motor shaft or a sleeve seated thereon. In these cases, the cam is driven, and the action of the cam being raised off from the further driven drive part is monitored.

In some embodiments, the toothbrush includes an adjusting device. The adjusting device adjusts the upper desired value and/or the lower desired value of the contact pressure. The adjusting device can change the bias effected by the prestressing device. Thus, because of the adjusting device, it is possible to change the point at which the follower part stops following the drive movement of the drive part to the full extent. On the other hand, the adjusting device also makes it possible to change the point at which the follower part is fully uncoupled from the drive part.

The signal representing the extent of coupling may be evaluated in different ways. In some embodiments, a filter evaluates the on/off signal, which represents the extent of coupling between the follower part and drive part. In some such cases, the sensor has a filter circuit, the input side of which is connected to the coupling-sensing arrangement.

In some cases, the on/off signal that specifies the extent of coupling is fed into a computing unit, preferably a microcontroller. The computing unit measures the duty cycle directly and, depending on the threshold, activates an indicator.

In some cases, an acoustic or optical device is provided as the indicator that indicates the contact pressure to the user. In some such cases, an LED display indicates the contact pressure.

DETAILED DESCRIPTION OF DRAWINGS

Figure 1:
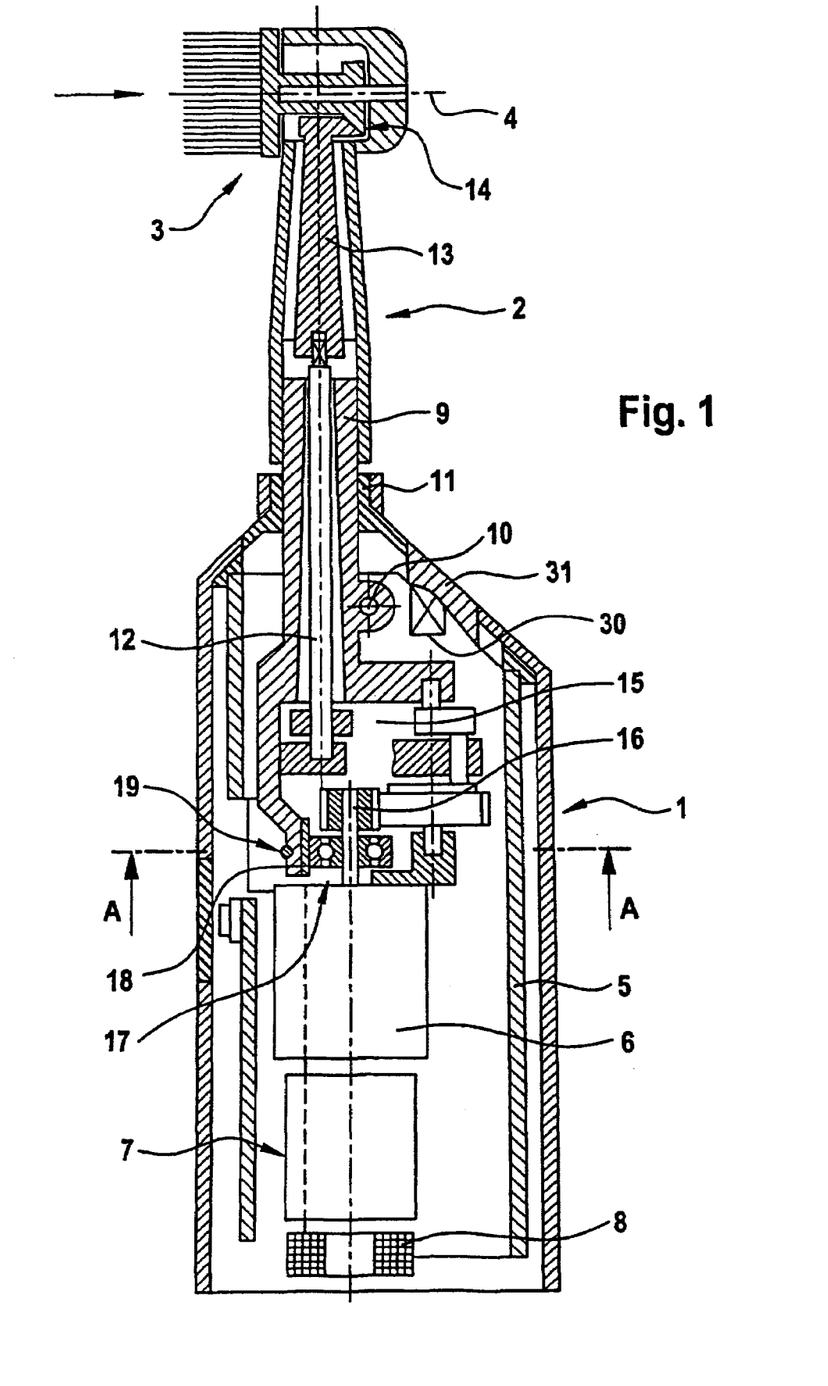
FIG. 1 is a diagrammatic view of an electric toothbrush according to one embodiment of the invention.

Referring to FIG. 1, an electric toothbrush has a handle 1, to which a brush-head carrier 2 is releasably attached. A brush head 3 is arranged at the end of the brush-head carrier 2. The brush head 3 is mounted on the brush-head carrier 2 such that it can be rotated about an axis 4. The axis 4 is essentially perpendicular to the longitudinal axis of brush-head carrier 2.

A chassis 5 is disposed within the interior of the handle 1. Fastened onto chassis 5 are a drive motor 6, a storage battery 7, and other electronic components, for example, a charging coil 8. Furthermore, a rocker 9 is mounted on the chassis 5 such that it can be pivoted about a rocker axis 10. The rocker axis 10 essentially extends transversely to the longitudinal axis of handle 1. The rocker 9 projects out of handle 1. The brush-head carrier 2 may be releasably attached to the projecting end of rocker 9. As a result, brush-head carrier 2 can be rocked, along with rocker 9, about rocker axis 10. The annular space remaining between handle 1 and rocker 9 may be sealed by an elastic membrane 11 or the like, which allows the rocking movement about rocker axis 10.

A first drive shaft 12 is disposed within the interior of rocker 9. When brush-head carrier 2 is attached to handle 1, first drive shaft 12 engages in a rotationally fixed manner with a second drive shaft 13. The second drive shaft 13 then drives brush head 3 in rotation about axis of rotation 4 via a bevel-gear stage 14. The motor end of first drive shaft 12 is connected to drive motor 6 via a gear mechanism 15. The electric toothbrush further includes, within handle 1, a motor shaft 16 that projects out from drive motor 6. The continuous rotary movement of motor shaft 16 is converted into a rotary, oscillating movement of first drive shaft 12 by means of gear mechanism 15. The result is that brush head 3 is driven in rotation in a reciprocating manner.

In some embodiments, an essentially translatory stroke or picking movement of brush head 3 along axis 4 may be produced by the pivotable arrangement of rocker 9. The rocker 9 is seated on a cyclically movable drive part 17 (here, a cam), which is designed as an eccentric and is itself seated on motor shaft 16. The end of rocker 9 that is directed away from brush head 3 forms a follower part 18. The follower part 18 follows the curved surface and/or cyclic movement of cam 17, so that rocker 9 executes a reciprocating rocking movement. For this purpose, a prestressing device 19, e.g., a spring, biases follower part 18 of rocker 9 against cam 17. The biasing, via rocker 9, forces brush head 3 in the direction of its operating side, while cam 17, by way of its corresponding curved surface, forces brush head 3 in the opposite direction.

The cam 17 preferably is a rolling-contact bearing designed as an eccentric. The inner raceway of the rolling-contact bearing is seated on motor shaft 16. In some embodiments, the inner raceway is an eccentric. In some such cases, the outer raceway of the rolling-contact bearing executes a cyclic movement which, referring to FIG. 1, reciprocates from right to left. In an alternative embodiment, a conventional rolling-contact bearing is seated on an eccentric collar of motor shaft 16, and the rolling-contact bearing executes a corresponding oscillating movement and acts as an eccentric.

Figure 2:
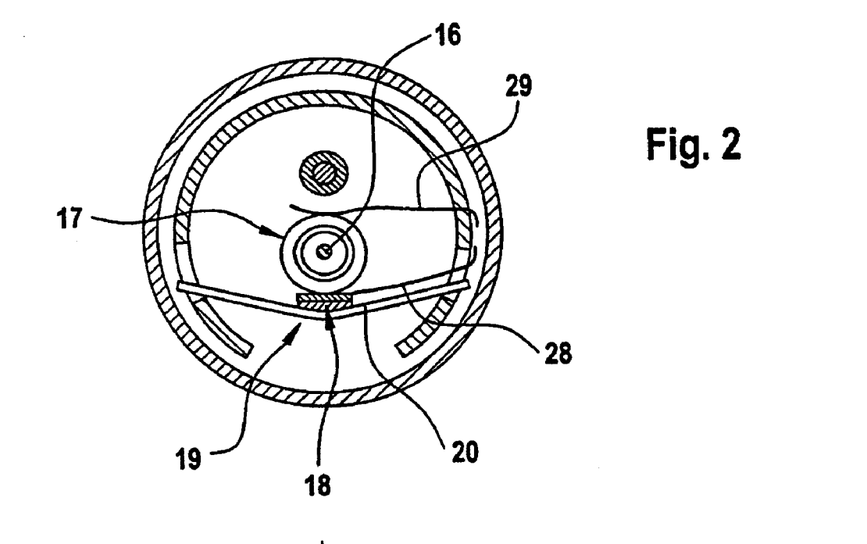
FIG. 2 is a cross-sectional view of the toothbrush from FIG. 1 along section line A—A in FIG. 1.

Referring now to FIG. 2, in some embodiments the toothbrush includes a clip spring 20. The clip spring 20 is supported on chassis 5, and it biases follower part 18 against cam 17.

In an alternative embodiment, a helical spring is provided instead of clip spring 20. In some embodiments, the clip spring 20 is supported directly on handle 1, rather than chassis 5, in order to force the follower part 18 of rocker 9 against cam 17.

Figure 3:
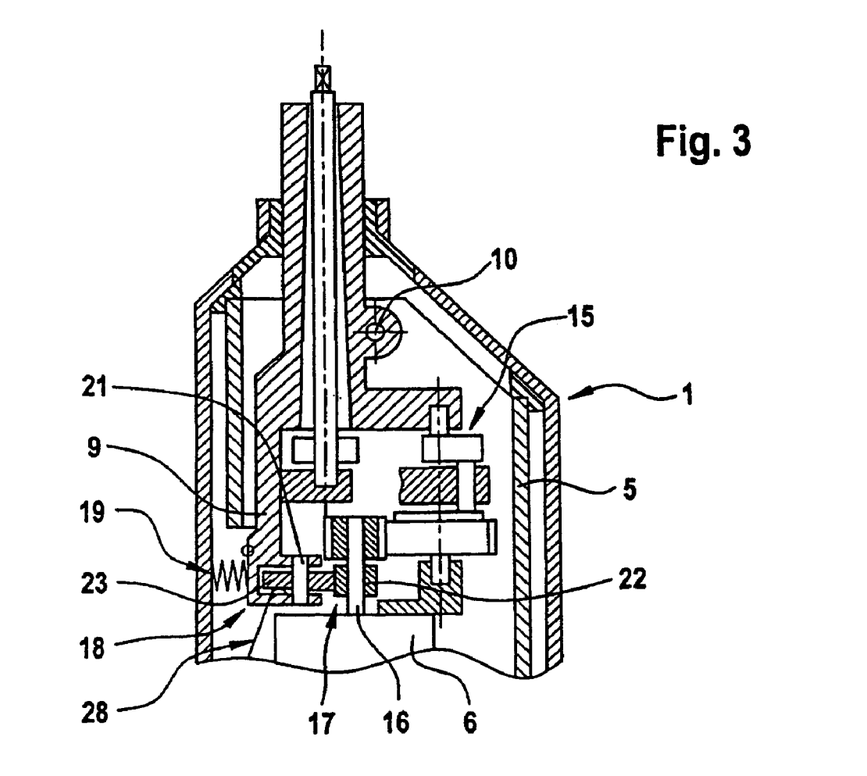
FIG. 3 is a diagrammatic view of a portion of one embodiment of the invention.

Referring now to FIG. 3, in some cases the rolling-contact bearing is arranged conversely. A pin 21 may be provided at the motor end of rocker 9, the pin extending parallel to motor shaft 16. Seated on pin 21 is a rotatable plate 23, which runs on motor shaft 16 or a sleeve 22 seated thereon. In order to achieve a cyclic drive movement of rocker 9, plate 23 may be designed as a cam plate and form an eccentric which runs on sleeve 22. Alternatively, sleeve 22 may be eccentric, with a preferably cylindrical plate 23 rolling thereon. The plate 23 may be designed, for example, as a rolling-contact bearing. The plate 23 and sleeve 22 may also be configured as a cam plate with a plurality of elevations over the circumference.

Figure 4:
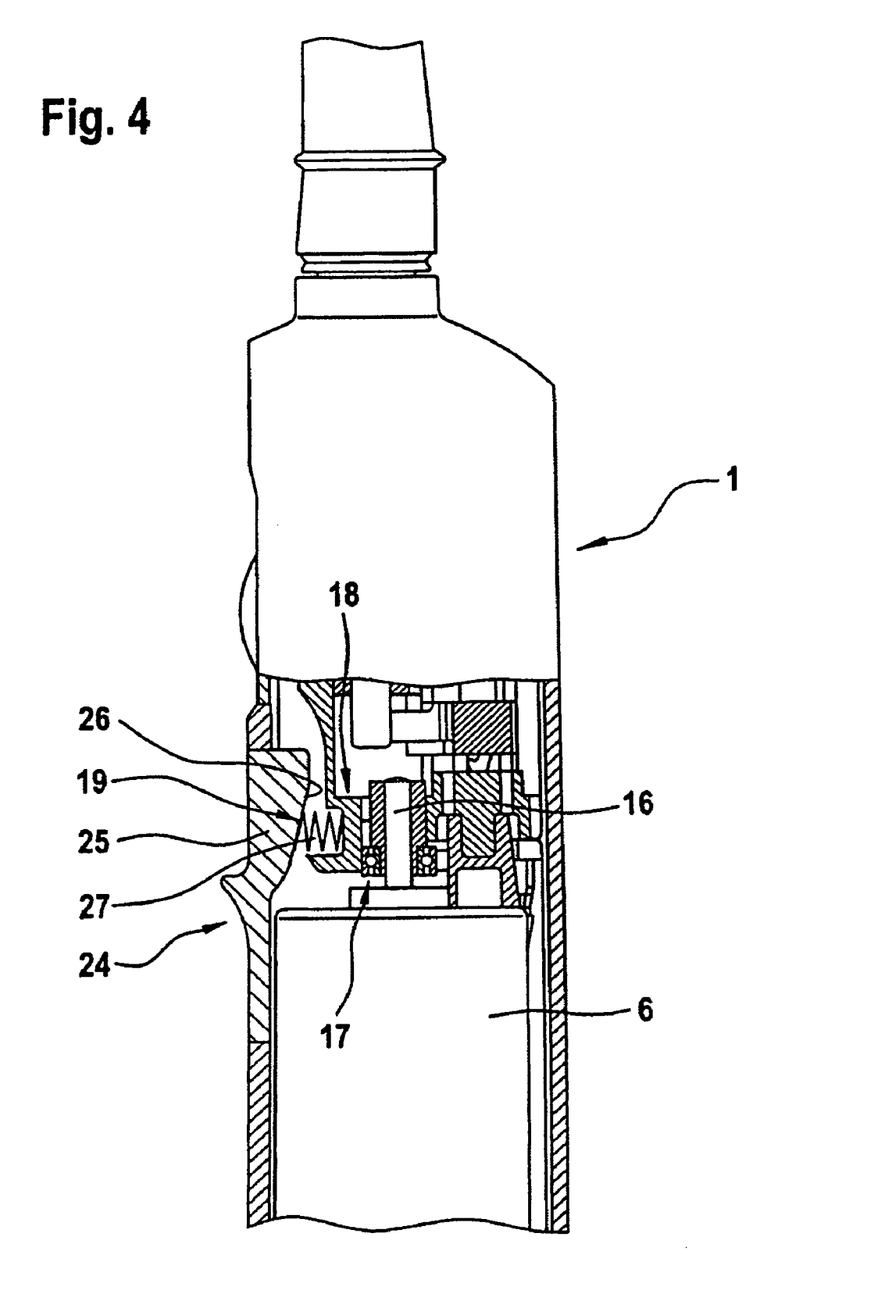
FIG. 4 is a diagrammatic view of a portion of one embodiment of the invention.

Referring now to FIG. 4, in one embodiment of the invention the toothbrush includes an adjusting device 24 that adjusts the force by which the follower part 18 of rocker 9 is biased against cam 17. The adjusting device 24 may be a switch, e.g., a sliding switch 25, which is mounted in a displaceable manner in handle 1. The sliding switch 25 can alter the effective length of biasing spring 27 by way of a wedge surface 26.

In operation, the rotary movement of motor shaft 16 causes rocker 9, via cam 17, to execute a reciprocating rocking movement. As a result, brush head 3 executes a corresponding reciprocating stroke movement. The biasing of follower part 18 in the direction of cam 17 is such that, in the non-loaded state of brush head 3, follower part 18 follows the cyclic drive movement of cam 17 to the full extent. In other words, the cyclic movement of cam 17 is fully converted into a corresponding rocking movement in rocker 9. This state lasts until brush head 3 is subjected to a contact pressure which corresponds to a lower desired value, as shown in FIG. 5a below.

Figure 5:
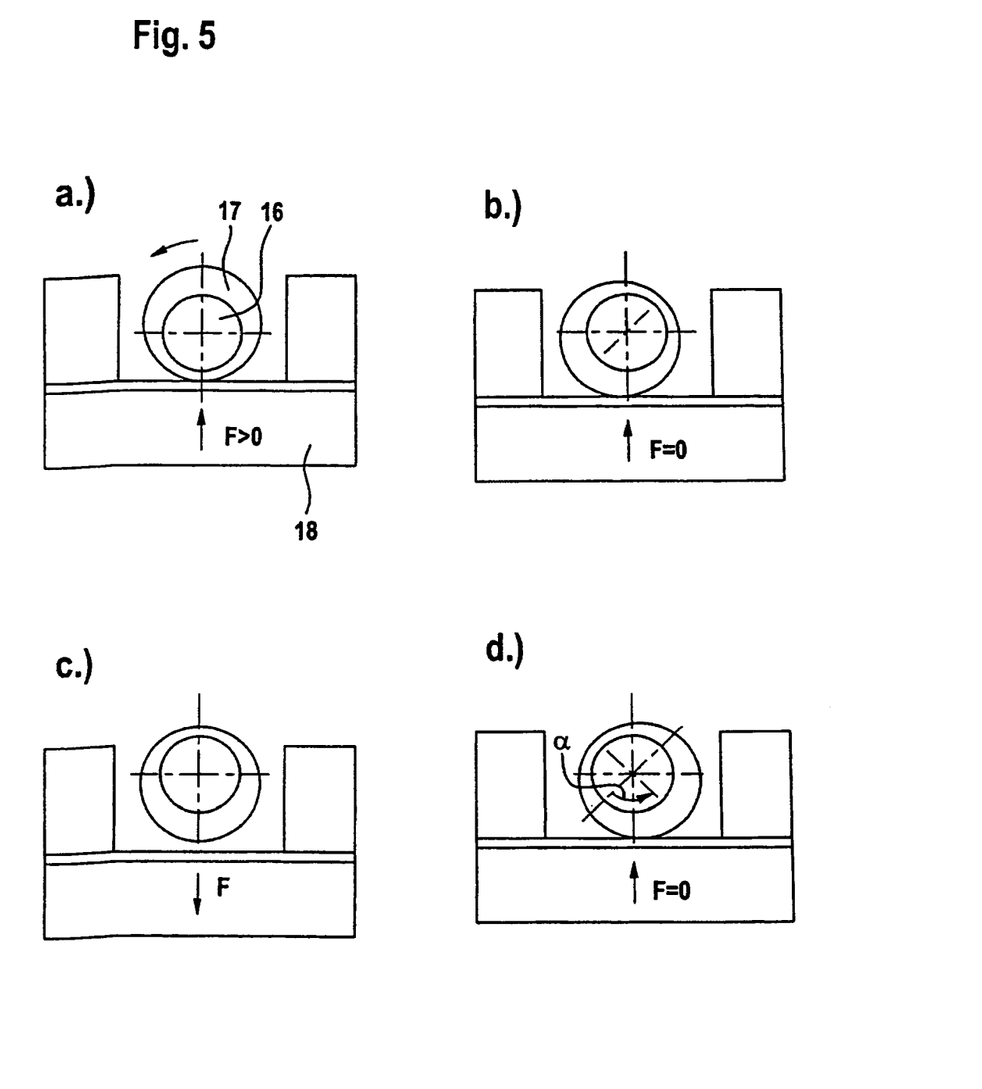
FIG. 5 is a schematic illustration of the extent of coupling, under varying contact pressures, between an eccentric and a follower part, according to one embodiment of the invention.

Referring now to FIG. 5a, the resultant contact-pressure force F between follower part 18 and cam 17 is greater than zero. The result is that there is always contact between follower part 18 and cam 17. If the contact-pressure force or cleaning force exceeds the lower threshold value, the resultant contact-pressure force F between follower part 18 and cam 17 is zero in a certain position of motor shaft 16. The result is that follower part 18 and cam 17 begin to disengage. The contact between the two parts is thus open.

Following a corresponding angle of rotation α, follower part 18 and cam 17 begin to engage again. For the rest of the rotation of the motor, the resultant contact-pressure force forces follower part 18 and cam 17 upon each other again, so that the contact is closed. The angle of rotation α at which the contact between follower part 18 and cam 17 is open increases as the cleaning force increases, until they are permanently raised off from one another. When they are permanently raised off from one another, the angle of rotation α then corresponds to 360 degrees. A minimum contact-pressure force of approximately 0.8 to 1 Newton should be maintained for an optimum teeth-cleaning result. This cleaning force, on the other hand, should not exceed a maximum value of approximately 1.8 to 2.3 Newtons, in order to prevent damage to the gums and teeth.

The biasing of prestressing device 19 preferably is such that, until the minimum desired force is achieved, follower part 18 and cam 17 are always in engagement and the contact is closed throughout the full revolution of the motor. The spring characteristic of prestressing device 19, the stroke of cam 17, and the inertia of gear mechanism 15 and the plug-on brush, as well as the frequency of rotation of motor shaft 16, may be selected such that, when the recommended maximum desired force has been achieved, the contact between follower part 18 and cam 17 remains permanently open.

Figure 7:
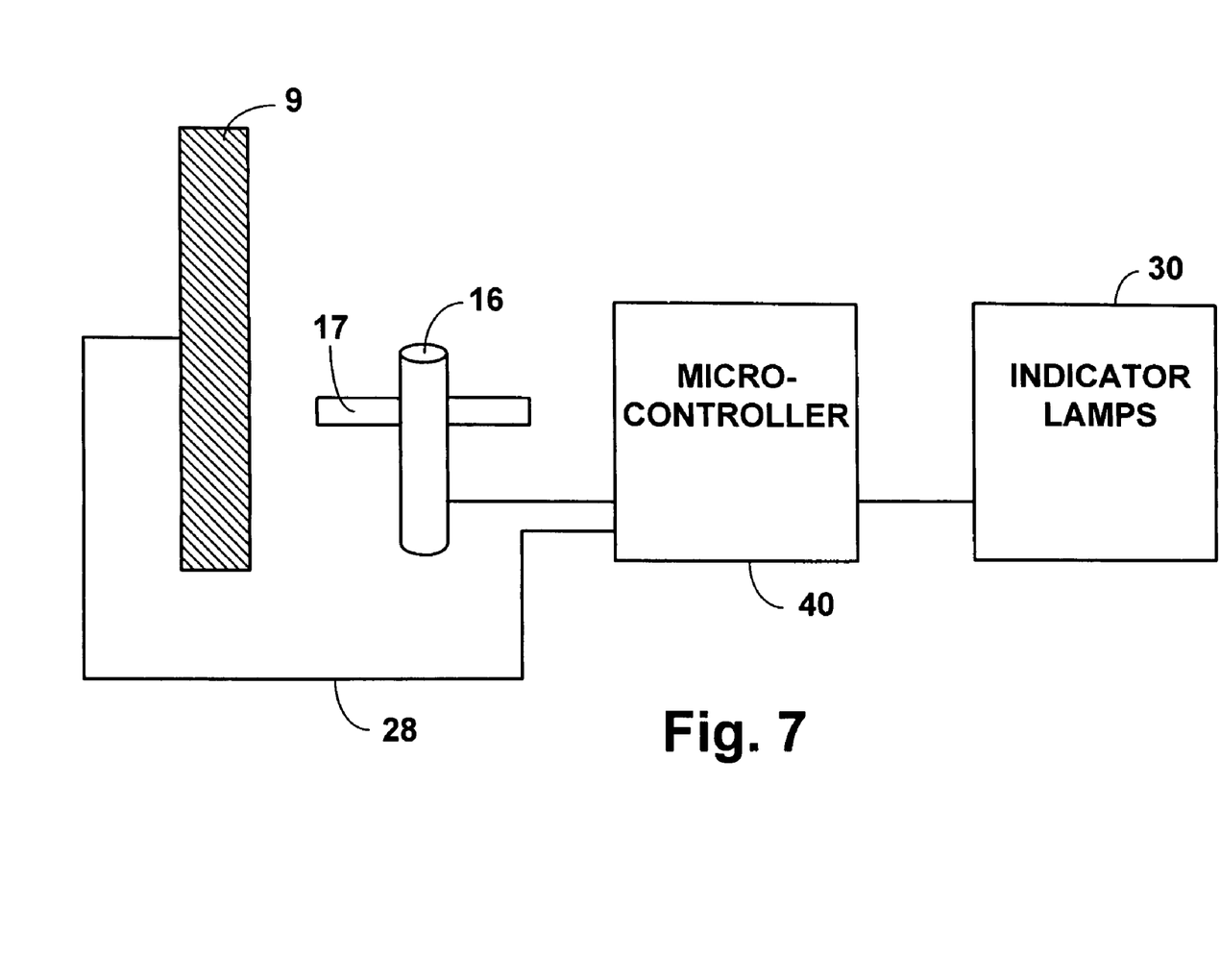
FIG. 7 is a schematic diagram of a sensing portion of one embodiment of the invention.

In order to produce a signal that represents the engagement state, the parts near cam 17 that roll or slide upon each other are made of metal. Referring now to FIGS. 1, 3 and 7, the metallic outer raceway of the ball bearing is connected in a conductive manner to motor shaft 16 directly, via the conductive ball cage and the likewise metallic inner raceway of the ball bearing. The motor shaft 16 is electrically connected to a computing unit 40 (here, a microcontroller). The contact surface of rocker 9, by means of which rocker 9 is seated on the outer raceway of the ball bearing, is likewise of metallic form. Hence, there is electrically conductive contact when rocker 9 and the ball bearing engage. As soon as rocker 9 is raised off from the ball bearing, the contact is opened and a corresponding signal is interrupted.

The rocker-side contact surface is likewise connected electrically to microcontroller 40 via a line 28. In some embodiments, rather than the outer ball-bearing raceway being connected to motor shaft 16 directly via the ball cage and the inner raceway, the outer ball-bearing raceway is directly electrically connected, for example by a contact spring 29, to microcontroller 40. The microcontroller 40 controls one or more preferably colored signal lamps 30. A transparent indicator 31 correspondingly illuminates the sensed contact-pressure force in different colors or by means of pulse signals.

Figure 6:
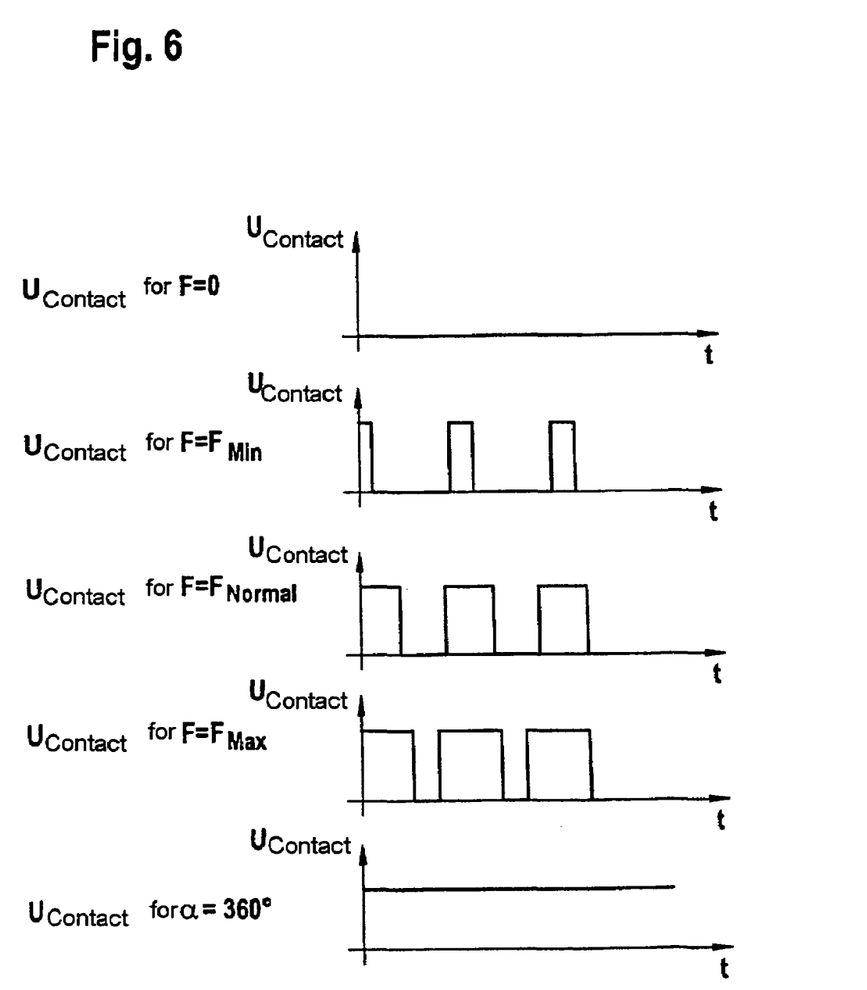
FIG. 6 is a schematic illustration of signal levels resulting from the varying contact pressures of FIG. 5.

In operation, the electric toothbrush has three operating ranges, corresponding to the selected biasing. Referring to FIG. 6*a*, as long as the contact pressure remains below the lower desired value and, accordingly, the follower part and cam are in constant contact, there is a constant signal level at a first level. Referring now to FIGS. 6*b*–6*d*, as soon as the contact pressure exceeds the lower desired value, but does not yet exceed the upper desired value, the follower part and cam are cyclically raised off from one another and brought into contact with each other. This motion results in a pulsating signal, as shown in FIGS. 6*b*, 6*c* and 6*d*. The signal switches between two signal states, the duty cycle changing in accordance with a change in the contact pressure. Referring to FIG. 6*b*, the signal is at the lower margin of the desired range of the contact pressure. Referring to FIG. 6*c*, the signal profile for a contact pressure in the center of the desired range is shown. Finally, referring to FIG. 6*d*, the signal profile for a contact pressure at the upper margin of the desired range is shown.

Referring to FIG. 6*e*, if the contact pressure exceeds the upper desired value, then there is a constant signal level. However, this constant signal level is at a different level from that in which the contact pressure has dropped below the lower threshold value. When the upper limit is exceeded, rocker 9 is raised off permanently from cam 17.

Referring now to FIG. 7, if the contact pressure is in the desired range, it is possible for the contact pressure to be determined in quantitative terms from the duty cycle of the signal changes. The duty cycle may be measured directly with the aid of microcontroller 40, which activates the colored signals lamps 30. Alternatively, a filter circuit can make an evaluation by comparing the signal according to FIGS. 6*b*–6*d* with threshold values via comparators.

What is claimed is:

1. An electric toothbrush comprising:
 a brush head;
 a drive that produces an oscillating motion in the brush head, wherein the drive includes a cyclically movable drive part and a follower part connected to the brush head, and wherein the follower part is movably biased toward the drive part; and
 a sensor that senses the contact between the drive part and the follower part.

2. The toothbrush of claim 1, wherein the sensor includes a pressure-determining circuit.

3. The toothbrush of claim 2, further comprising an indicator that is connected to the pressure-determining circuit and that displays the contact pressure.

4. The toothbrush of claim 2, wherein the pressure-determining circuit measures the contact pressure based on a duty cycle, and wherein the duty cycle is a function of the portion of the drive part' movement cycle when the follower part is coupled to the drive part, and the portion of the movement cycle when they are uncoupled.

5. The toothbrush of claim 2, wherein the pressure-determining circuit includes a filter circuit having an input side that is connected to the sensor.

6. The toothbrush of claim 2, wherein the pressure-determining circuit includes a computing unit.

7. The toothbrush of claim 6, wherein the computing unit comprises a microcontroller.

8. The toothbrush of claim 7, further comprising an indicator that is connected to the microcontroller and that signals the contact pressure.

9. The toothbrush of claim 8, wherein the indicator comprises an LED display.

10. The toothbrush of claim 1, wherein the follower part is biased against the drive part by a spring.

11. The toothbrush of claim 10, wherein the spring causes the follower part to couple to the drive part for a portion of the duration of the movement cycle of the drive part.

12. The toothbrush of claim 1, wherein the sensor senses electrically conductive contact between the follower part and the drive part.

13. The toothbrush of claim 1, wherein the sensor comprises a switch that is formed by the follower part and the drive part.

14. The toothbrush of claim 1, wherein the drive comprises a stroke drive that produces a translatory stroke movement in the brush head.

15. The toothbrush of claim 1, wherein the drive part comprises a cam.

16. The toothbrush of claim 1, further comprising a rocker.

17. The toothbrush of claim 1, further comprising an adjusting device that adjusts the force of the follower part against the drive part.

18. The toothbrush of claim 16, wherein a portion of the rocker forms the follower part.

19. The toothbrush of claim 18, wherein the rocker has a first end that is connected to the brush head and a second end that is biased against the drive part.

* * * * *

UNITED STATES PATENT AND TRADEMARK OFFICE
CERTIFICATE OF CORRECTION

PATENT NO. : 7,120,960 B2  Page 1 of 1
APPLICATION NO. : 10/310599
DATED : October 17, 2006
INVENTOR(S) : Alexander Hilscher and Hansjorg Reick

It is certified that error appears in the above-identified patent and that said Letters Patent is hereby corrected as shown below:

Column 8, Claim 4, Line 9:

Delete "part' " and insert --part's--

Signed and Sealed this

Fourth Day of September, 2007

JON W. DUDAS
*Director of the United States Patent and Trademark Office*